United States Patent [19]
Gaud et al.

[11] Patent Number: 4,584,521
[45] Date of Patent: Apr. 22, 1986

[54] METHOD OF DETECTING THE DEFECTS IN A DIELECTRIC COATING AT THE SURFACE OF AN ELECTRICALLY CONDUCTIVE UNDERLAYER

[75] Inventors: Jacques V. Gaud, Perly; Michel Kornmann, Grand-Lancy, both of Switzerland

[73] Assignee: Battelle Memorial Institute, Geneva, Switzerland

[21] Appl. No.: 514,813

[22] PCT Filed: Oct. 11, 1982

[86] PCT No.: PCT/CH82/00109
§ 371 Date: Jun. 15, 1983
§ 102(e) Date: Jun. 15, 1983

[87] PCT Pub. No.: WO82/01514
PCT Pub. Date: Apr. 28, 1983

[30] Foreign Application Priority Data
Oct. 16, 1981 [CH] Switzerland .................. 6619/81

[51] Int. Cl.⁴ .................. G01R 31/00; G01R 31/12
[52] U.S. Cl. .................. 324/54
[58] Field of Search .................. 324/326, 51, 52, 54

[56] References Cited
U.S. PATENT DOCUMENTS

| | | | |
|---|---|---|---|
| 1,297,929 | 3/1919 | Taylor | 324/52 |
| 2,651,021 | 9/1953 | Hays | 324/52 |
| 2,860,304 | 11/1958 | Hall | 324/52 |
| 3,210,655 | 10/1965 | McGlasson | |
| 3,526,831 | 9/1970 | Smith | 324/326 |

FOREIGN PATENT DOCUMENTS

| | | |
|---|---|---|
| 436753 | 3/1973 | Australia . |
| 1338781 | 8/1963 | France . |
| 2354563 | 1/1978 | France . |
| 2015165 | 9/1979 | United Kingdom . |

*Primary Examiner*—Reinhard J. Eisenzopf
*Assistant Examiner*—Jose M. Solis
*Attorney, Agent, or Firm*—Karl F. Ross; Herbert Dubno

[57] ABSTRACT

The method consists in placing a conductive underlayer (1) coated by a dielectric layer (5) in a conductive medium in which an excitation electrode (2) is positioned at a distance from this underlayer (1). This underlayer (1) and this excitation electrode (2) are being connected to the corresponding terminals of an alternative-current generator (4) and between this electrode (2) and this underlayer (1) one interposes a catcher coil (6) oriented in a plan perpendicular to the electric field lines and a potential-measuring electrode (7) in the opening of said coil (6) and one determines the impedance resulting from the voltages and currents detected.

2 Claims, 4 Drawing Figures

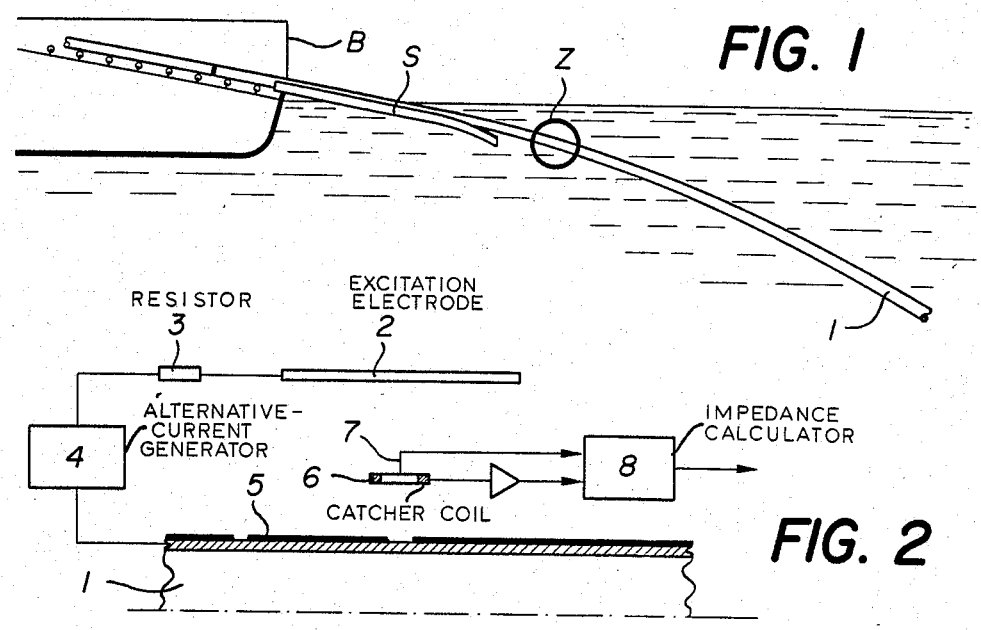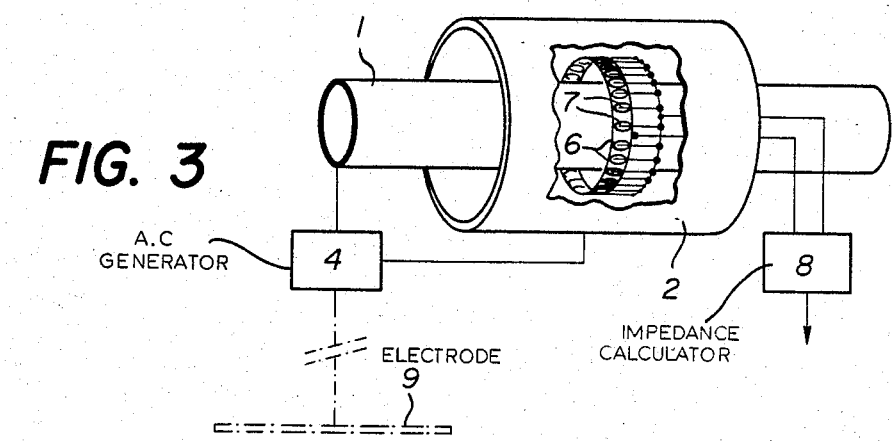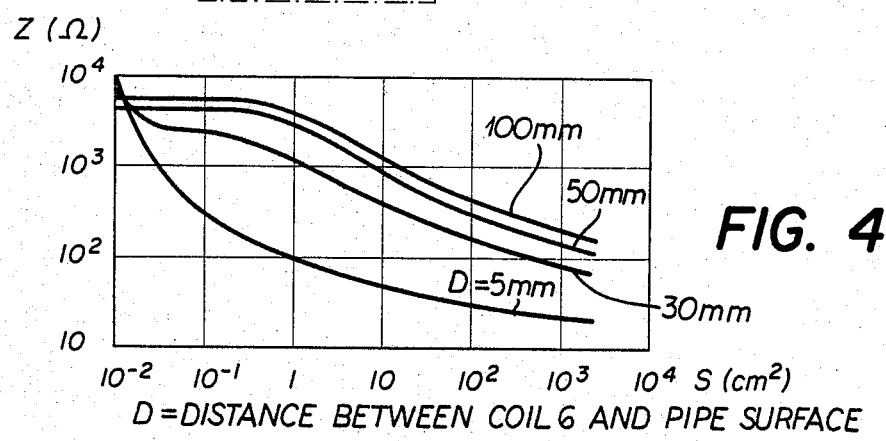

METHOD OF DETECTING THE DEFECTS IN A DIELECTRIC COATING AT THE SURFACE OF AN ELECTRICALLY CONDUCTIVE UNDERLAYER

CROSS REFERENCE TO RELATED APPLICATION

The present application is a national phase application of PCT/CH82/00109 filed Oct. 11, 1982 and based in turn upon a Swiss national application No. 6619/81-9 filed Oct. 16, 1981 under the International Convention.

FIELD OF THE INVENTION

The present invention relates to a method of detecting the defects in a dielectric coating at the surface of an electrically conductive underlayer. This method is especially applicable to the detection of defects in the coating of submersed pipelines.

BACKGROUND OF THE INVENTION

It is known that these pipelines are provided with double protection against corrosion, one being the protection afforded by a coating layer of plastic material and the other the protection provided by cathodic polarization of the steel of the pipeline with respect to the sea water, this cathodic polarization being obtained, for instance, by arranging zinc anodes at given intervals around the pipeline, the polarization taking place between the zinc bracelets and the portions of the steel pipe not protected by the coating as a result of the deterioration of this coating.

Although it is rather easy to detect and correct coating defects occurring before the positioning of the pipeline, no provisions are made to correct damage suffered during laying of the pipeline. Under these conditions the zinc bracelets are arranged at intervals based on a statistical evaluation of the defects.

It has been already proposed to control the cathodic protection after the positioning of the pipeline, either by measuring the potential of the pipe with respect to the surrounding medium, or by measuring the protection currents circulating either in the pipe or in the surrounding medium. The measurement of the protection current can not be done during the positioning because of the perturbations generated by the parasitic currents originating from the numerous electrical machines used during the positioning of a pipeline, such as the welding currents.

There are methods already known in electrochemistry to study the condition of the surface by measuring the impedance of a surface submerged in a conductive medium by using an electrode excited by an alternating-current generator of average frequency and a potential-measuring electrode located very closely to the studied surface. The impedance is a result of the relation between the measured potential and the excitation current delivered. Such a method of measurement is applicable only to an examination taking place very close to the surface (only a few tens of microns), due to the fact that when the distance is of the order of millimeter, the low resistivity of the medium especially when this medium is sea water has a tendency to equalize the potential between the excitation electrode and the substratum, so that it is no longer possible to measure the variations in impedance.

OBJECT OF THE INVENTION

The object of the present invention is to measure the surface impedance at a distance from the underlayer sufficient to allow relative displacement of the underlayer and an excitation electrode, in order to measure continuously big and small defects, even if they are close to each other.

SUMMARY OF THE INVENTION

To accomplish this object the invention provides a method of detecting defects in a dielectric coating at the surface of an electrically conductive underlayer, according to which an excitation electrode is positioned at a distance from said underlayer on the side thereof covered by said coating, this electrode and this underlayer being placed in a common electrically conductive medium and the potentials corresponding to said underlayer and said electrode are carried to the terminals of an alternating-current generator. This method is characterized by the fact that a catcher coil is oriented essentially perpendicular to the electric field lines and an electrode for measuring the potential is positioned in the opening of said coil and one determines the impedance resulting from the voltages and currents detected by said measuring electrode and said catcher coil.

The advantage of this method is that it is particularly well suited for the control of the coating of submerged pipelines during their positioning, due to the fact that the high-frequency currents which can be used are insensitive to the surrounding parasite currents, such as welding currents, and that the detection can be achieved at a distance from the surface of the underlayer sufficient to allow for a continuous control as the positioning of the pipeline progresses when the pipe enters the sea water and leaves the stinger which is an element guiding the pipe extending at the rear of the barge used for the positioning of the pipeline. As a result, this method creates the possibility to achieve control at a point where the pipe has lost all contact with the pipeline positioning installation capable of causing deterioration of the protective coating. It is therefore possible by using this method to measure the surface of the pipe not protected by the coating of plastic material and to distribute the zinc anode as a function of the required protection by cathodic polarization or to repair the coating of the pipe when the uncovered surface of the steel passes a certain limit.

BRIEF DESCRIPTION OF THE DRAWING

The accompaying drawing shows schematically the use of the method of the invention. In the drawing:

FIG. 1 is an elevational view of a barge for positioning of pipelines showing the control area of the pipe.

FIG. 2 schematically shows the principles of the detection device.

FIG. 3 schematically shows the application of the method for detecting defects in the coating of a tube.

FIG. 4 is a graph of the impedance measured with respect to the extent upon the defects and in dependence of the distance between the underlayer and the catcher coil.

SPECIFIC DESCRIPTION

FIG. 1 simply shows the area Z in which it is desirable to perform the control of the coating of a substratum consisting in this example of a pipe 1. One can see that this area is immersed and is situated at the exit end of the stringer S constituting a guiding surface for the pipe and located at the rear of the barge B.

The principle on which the method is based is explained in connection with the detection device shown in FIG. 2. This device comprises an excitation electrode 2 located at a certain distance from the pipe 1 and connected via a resistance 3 to a terminal of an alternating-current generator 4, whose other terminal is connected to the pipe 1 surrounded by a dielectric coating 5. A toroid catcher coil 6 is located between the excitation electrode 2 and the wall of the pipe 1, essentially parallel to the underlayer so that the current lines developing between the excitation electrode 2 and the pipe 1 cross the opening of the toroid catcher or sensing coil 6. This way the catcher coil measures the current component perpendicular to the pipe. Indeed, if one accepts for instance a constant current density i having a direction forming an angle with the axis of revolution of the toroid coil, the current crossing the opening of this coil is:

$$I = I_0 \cos \alpha$$

where $I_0 = iS$, S being the area of this opening.

Due to the directivity of the measurement of the current by the catcher coil 6 it is possible to obtain significant information regarding the electrical behavior of the portion of the underlayer surface located opposite this coil.

An electrode 7 for measuring the potential is placed in the plane of the catcher coil 6 in a manner insuring absolute significance of the measuring of the current. These signals voltage/current are collected by a receiving member 8 which calculates the value of the impedance existing between the plan of the torus and the surface of the underlayer. This directivity of the measuring is precisely the reason the method is capable to detect small and large defects located side by side due to the fact that the detecting coil 6 measures only the current component perpendicular to the surface of the underlayer. This directivity is further enhanced by making the excitation electrode 2 as big as possible.

The frequency of the feeding current also influences the sensitivity of the current measuring. For instance a frequency of 10,000 Hz feeding ferrite-core toroid coils with an initial high permeability allows to attain sensitivities on the range of 10 to 100 mV/mA.

A series of tests have been performed in a simulated sea water environment on a pipe segment coated with a layer of polyethylene having a thickness of 3 mm whereby certain portions have been eliminated to uncover the steel of the pipe. These portions of uncovered surface have a diameter of between 2 and 5 mm, 10×2 cm or extend over a complete portion of the tube. To simulate the real conditions a zinc anode is associated with the pipe.

In FIG. 3 the electrode 2 is shown to be cylindrical and the toroidal sensing coil 6 part of an array of such coils uniformly spaced about the periphery of the pipe 1.

TABLE

| Area tested | Distance in cm | Impedance (ohms) |
| --- | --- | --- |
| Polyethylene | 0.5 cm | 9500 |
|  | 3 cm | 8000 |
| S = 0 | 5 cm | 6200 |
|  | 10 cm | 7100 |
| Defect φ 2 mm | 0.5 cm | 1100 |

TABLE-continued

| Area tested | Distance in cm | Impedance (ohms) |
| --- | --- | --- |
|  | 3 cm | 4700 |
| S = 3.10$^{-2}$ cm$^2$ | 10 cm | 7000 |
| Defect φ 5 mm | 0.5 cm | 350 |
|  | 3 cm | 2400 |
| S = 0.2 cm$^2$ | 10 cm | 7000 |
| Defect 2 × 10 cm | 0.5 cm | 50 |
|  | 3 cm | 375 |
| S = 20 cm$^2$ | 5 cm | 600 |
|  | 10 cm | 750 |
| Uncovered | 0.5 cm | 20 |
| Surface | 3 cm | 70 |
| S → ∞ | 5 cm | 100 |
|  | 10 cm | 180 |

Two different diameters for the toroid catcher coil 6 have been tested, namely one of 2.5 cm and the other of 1 cm, each having 200 turns. Using a 10 kHz current the measured sensitivities are respectively 45 and 40 mV/mA. The excitation electrode is fed by a current limited to 150 mA.

The measurements have been taken over the entire length of the pipe, in contact with the coating at a distance of approximately 5 mm from the underlayer, respectively at 30, 50 and 100 mm. The above table shows the results obtained with the toroid catcher coil having a diameter of 2.5 cm.

The diagram in FIG. 4 gives a graphical representation of these results whereby the distance between the catcher coil 6 and the underlayer is the parameter.

One can see that at a distance of 5 mm defects in the range of $10^{-2}$ cm$^2$ are detectable, at 3 cm defects of $10^{-1}$ cm$^2$ are still detectable, at 5 cm it is possible to detect defects over 1 cm$^2$, while at 10 cm the limit lies between 5 and 10 cm$^2$.

FIG. 3 represents an application of the method according to the invention in the detection of the coating of a pipeline immersed in sea water. This device corresponds exactly to the schematic representation of the principle in FIG. 2, a series of toroid catcher coils 6 being distributed annularly around the pipe 1 and connected to a multichannel receiving element 8 as well as the potential measuring electrodes 7 located in the plan of each catcher coil. The excitation electrode 2 comprises a ring connected to one of the terminals of the alternative current generator 4 whose other terminal is connected to the pipe 1. It has to be noted that this detection method is also applicable to the detection of defects of pipelines after their positioning in the sea. In this case, instead of connecting the source of the alternative current 4 to the duct 1 as this can be easily done during positioning, the second terminal of the generator 4 can be connected to an electrode 9 located very far from the pipe 1, at a distance 50 to 100 times bigger than that between the excitation electrode 2 and the pipe 1 which permits to obtain practically the same results as by bringing the pipe directly to the potential of the mass of the alternative current generator.

It is known that in a good number of cases the immersed pipelines are covered with a layer of concrete in order to give a weight superior to the ascending pressure of the displaced volume of water. Tests have been performed to evaluate the influence of the concrete layer on the measuring and especially the influence of the resistivity of the concrete. The resistivity of the concrete can vary widely depending on its composition, preparation and age and on its water content. The resistivity in bulk of the concrete 10 days after its preparation lies between 5000 ohms.cm and 0.5 megohms.cm. After 90 days the resistivity can reach values in the range of 500 megohms.cm and the resistivity of furnace-dried concrete can increase to $10^6$ megohms.cm.

But in the case of immersed pipelines, the resistivity depends on the water absorption. Test have shown that the resistivity decreases by approximately 1 megohm.cm to 10,000 ohms.cm a few hours after the sample has been immersed in the simulated sea water. These values have to be compared with the resistivity of the sea water which is in the range of 30 ohms.cm. However, the steel reinforcement renders the situation more complex.

Various measuring tests have been carried out with steel tubes coated with polyethylene as aforementioned and with a 5 cm layer of concrete with or without reinforcement by a grating of steel wire of 1.6 mm with mesh sizes of 2.5×2.5 cm. The concrete was prepared in a proportion of 450 Portland cement to 1 m³ sand (0-11) and 350 kg Portland cement to 1 m³ sand (0-20). The simulated defects were obtained by perforations of 6 to 12 mm in diameter.

The measuring was carried out in the immediate vicinity of the concrete layer or at 5 to 6 cm from the steel pipe. The impedances measured with defects in the concrete layer as well as in the dielectric adjacent to the pipe are in the same range as those measured without concrete at the same distance from the steel pipe.

We claim:

1. A method of detecting defects in a dielectric coating on the surface of electrically conductive pipe adapted to serve as a submerged pipeline, comprising the steps of:
    feeding said pipe substantially continuously below the surface of a body of water through a submerged zone above a floor of said body of water and below the surface of said body of water;
    spacedly juxtaposing said pipe with an excitation electrode extending only along said zone with said pipe in said body of water so that said pipe moves progressively past said excitation electrode through said zone;
    applying an alternating current across said pipe and said excitation electrode;
    disposing between said electrode and said pipe in said body of water at least one ferrite-core toroidal current sensing coil with a plane of said coil substantially perpendicular to a perpendicular from said surface of said pipe whereby said coil measures electric current passing substantially along said perpendicularly between said pipe and said electrode;
    providing a potential detecting electrode in an opening of said coil; and
    calculating the impedance of an electric current path between said surface of said pipe and said excitation electrode in response to the current measured by said coil and electrical potential detected by said potential detection electrode.

2. The method defined in claim 1 wherein said pipe is passed through said excitation electrode which is tubular and surrounds said pipe in said zone, and a plurality of such coils disposed around said pipe are provided in said zone between said excitation electrode and said pipe.

* * * * *

UNITED STATES PATENT AND TRADEMARK OFFICE
CERTIFICATE OF CORRECTION

PATENT NO. : 4,584,521

DATED : 22 April 1986

INVENTOR(S) : Jacques VERMOT-GAUD

It is certified that error appears in the above-identified patent and that said Letters Patent is hereby corrected as shown below:

In the heading, left column, item [75], the inventor's name should read:  -- Jacques VERMOT-GAUD --.

Item [19] "Gaud et al." should read --Vermot-Gaud et al--.

Signed and Sealed this

Twenty-ninth Day of July 1986

[SEAL]

Attest:

DONALD J. QUIGG

Attesting Officer

Commissioner of Patents and Trademarks